United States Patent [19]

Kumano

[11] 4,035,513

[45] July 12, 1977

[54] WATER-IN-OIL EMULSIFIER COMPOSITIONS

[75] Inventor: Yoshimaru Kumano, Yokohama, Japan

[73] Assignee: Shiseido Co., Ltd., Tokyo, Japan

[21] Appl. No.: 624,015

[22] Filed: Oct. 20, 1975

[30] Foreign Application Priority Data

Oct. 19, 1974 Japan .............. 49-120554

[51] Int. Cl.$^2$ .............................. A61K 7/48
[52] U.S. Cl. .................. 424/359; 424/168; 424/172; 424/177; 424/319
[58] Field of Search ............ 424/359, 168, 172, 70, 424/177

[56] References Cited

U.S. PATENT DOCUMENTS

| | | | |
|---|---|---|---|
| 2,129,836 | 9/1938 | Goodman | 424/70 |
| 2,173,203 | 9/1939 | Harris | 424/70 X |
| 2,192,907 | 3/1940 | Harris | 424/70 X |
| 2,372,159 | 3/1945 | Lavan | 424/70 X |
| 2,382,398 | 8/1945 | Cordero | 424/70 X |
| 2,436,818 | 3/1948 | Musher | 424/359 X |
| 3,016,334 | 1/1962 | Lewis | 424/359 X |
| 3,907,580 | 9/1975 | Van Ham | 424/359 X |

FOREIGN PATENT DOCUMENTS

| | | | |
|---|---|---|---|
| 676,612 | 12/1963 | Canada | 424/359 |
| 30,715 | 11/1966 | Japan | 424/308 |

Primary Examiner—Dale R. Ore
Attorney, Agent, or Firm—Sughrue, Rothwell, Mion, Zinn and Macpeak

[57] ABSTRACT

A water-in-oil emulsifier composition suitable for providing stable cosmetics such as creams, milky lotions, sticks, etc., comprises a mixture of: (A) a partial ester of a polyhydric alcohol having at least 3 hydroxyl groups and a fatty acid, the partial ester being in the liquid state at room temperature; and (B) an aqueous solution of an amino acid or a salt thereof.

15 Claims, No Drawings

WATER-IN-OIL EMULSIFIER COMPOSITIONS

BACKGROUND OF THE INVENTION

1. Field of the Invention

The present invention relates to an emulsifier composition containing an amino acid or a salt thereof possessing excellent effects on the skin and providing stable water-in-oil emulsions. Further, the present invention relates to a cosmetic containing the same.

2. Description of the Prior Art

The amino acids used as a component for the emulsifier compositions of this invention are one of the three important nutrients which serve as an energy source for body activities and are an important element to life, in particular, being indispensable for the formation of cell proteins.

The amino acids are not only an important element in skin nutrition, but are also important to skin tissue in general and the moisture retaining (water-retaining) capability thereof. It has been confirmed that these amino acids are present in a considerable amount in the material called the "National Moisturizing Factor" which exists in the keratin of the skin.

However, one problem encountered in utilizing these amino acids which possess such important effects in the field of cosmetics is that they have difficulty in skin penetration since they are highly soluble in water. In this connection, since the emulsifier composition of this invention comprising a mixture of an aqueous solution of an amino acid or a salt thereof and a partial ester of a polyhydric alcohol and a fatty acid in a proper mixing ratio forms a fat-soluble complex, it is found that the amino acid is absorbed by the skin to exhibit the aforesaid effects and functions on the skin.

Recently, it has been proposed to synthesize an esterification product of an amino acid and to use the above-described esterification product as surface active agents, but the present invention has the feature that an amino acid itself is used, and further, since the emulsifier composition containing the amino acid forms a lipophilic complex, the amino acid itself shows high stability in cosmetics such as creams, etc., and does not cause changes in the properties of the cosmetic.

The range of use of water-in-oil emulsions has been narrowed recently by oil-in-water emulsions, but the former are still widely utilized in the cosmetic and medication fields for cold creams, cleansing creams, hand creams, ointments, etc. In a conventional water-in-oil type emulsion using nonionic surface active agents, a large amount of a highly lipophilic emulsifier is compounded with a small amount of a hydrophilic emulsifier and a larger amount of oily components at an empirically determined ratio. Such water-in-oil type emulsions are subjected to some defects in that the emulsions formed become unstable due to phase separation, and as it is difficult to retain a large proportion of water in the internal phase of the emulsions, it is difficult to achieve stable emulsions. To increase the stability of such water-in-oil emulsions, various means have been attempted such as increasing the proportion of the oil phase corresponding to the external phase of the emulsion, increasing the viscosity of the emulsion by adding a hydrocarbon wax, a hydrocarbon aerogel, a metallic soap, a low molecular weight polyethylene, etc., and adding lanolin, or a derivative thereof, such as lanolin, lanolin alcohol esters, ethylene oxide adducts of lanolin alcohol, cholesterol or cholesteryl esters, to the emulsion. However, water-in-oil emulsions prepared by such methods have faults, i.e., in addition to the above-mentioned instability, they are generally grease-like and sticky, which reduces the usability and appearance thereof, and they also have a stimulative or allergic effect on the skin.

On the other hand, the novel water-in-oil emulsifier composition of this invention obtained by blending the aforesaid component (A), the partial ester of a polyhydric alcohol and a fatty acid, and component (B), an aqueous solution of the amino acid or salt thereof overcomes the aforesaid undesirable difficulties with conventional water-in-oil type emulsions and provides water-in-oil emulsions which are stable and safe for use on the skin. The water-in-oil type emulsifier composition of this invention obtained by properly compounding the aforesaid components is believed to strengthen the oil-water interfacial layers. While the details of the mechanism involved are not yet completely clear, it is believed that a water-insoluble complex possessing a hydrophobic external phase and a hydrophilic internal phase is formed, and that the complex strengthens the oil-water interfacial layers of the emulsion.

Thus, in order to provide, for example, stable water-in-oil type creams by conventional techniques, it is necessary that the external oil phase be higher than 75% but by using the emulsifier compositions of this invention, stable water-in-oil type creams can be prepared with the proportion of the internal water phase increased to 30-70, preferably 50-70, by volume, and hence water-in-oil emulsions possessing a large proportion of water and a wet, fresh feeling can be obtained.

A water-in-oil emulsifier composition obtained by mixing oleic acid monoglyceride an sorbitol is disclosed in U.S. Pat. No. 3,536,816, but the water-in-oil emulsifier composition of the present invention is superior to such a water-in-oil emulsifier composition in that the emulsion of this invention has a fresh feeling upon use, and the emulsions or creams of this invention have an excellent affinity to the skin. Furthermore, since the amino acid or a salt thereof activates the function of the skin glands, strengthens the flexible tissues of the derma and the skin tissues, and possesses an important element for improving the nutrition state of the skin, cosmetics comprising the emulsifier composition of this invention have the excellent merit that a large effect on skin physiology can be expected as compared with the aforesaid conventional technique of blending sorbitol.

As a result of various investigations, the inventor has succeeded in providing water-in-oil emulsifier compositions containing an effective amount of an amino acid or a salt thereof showing an excellent effect on the skin which can be used to prepare water-in-oil type emulsions having high stability and an excellent feel upon use, which are different from conventional emulsions of the same type.

SUMMARY OF THE INVENTION

One object of the present invention is to provide a water-in-oil emulsifier composition comprising:

A. at least one partial ester of a polyhydric alcohol having at least 3, preferably up to 6, hydroxyl groups in the molecule and a fatty acid having 16 - 18 carbon atoms which is in the liquid state at room temperature (e.g., about 0 - 35° C); and B. an aqueous solution containing at least one of an amino acid or a salt thereof, the ratio of component (B)

to component (A) being from 1 : 1 to 1 : 46 by weight, preferably from 1 : 2 to 1 : 15 by weight.

Another object of the present invention is to provide a cosmetic, such as a cream, milky lotion or stick cosmetic, containing 5 to 30% by weight of the above-described emulsifier composition.

DETAILED DESCRIPTION OF THE INVENTION

It is important the partial ester of a polyhydric alcohol and a fatty acid used for the emulsifier composition of this invention be in the liquid state at room temperature, since when a material in the solid state at room temperature, such as glycerol monostearate, sorbitan monostearate, etc., is mixed with an aqueous solution of an amino acid, they undergo phase separation to form two layers, which makes the formation of an effective emulsifier composition difficult.

The partial ester used in this invention can be formed from the following materials. The polyhydric alcohols used for preparing the partial ester are those which contain therein 3 to 6 hydroxyl groups, have 3 to 6 carbon atoms and are water-soluble, and examples of such polyhydric alcohols are glycerin, diglycerin, trimethylolethane, trimethylolpropane, pentaerythritol, sorbitan and sorbitol. The fatty acid used for forming the partial ester by the reaction thereof with the above-described polyhydric alcohol has 16 – 18 carbon atoms and examples of the fatty acid are oleic acid, linolic acid, ricinolic acid, isohexadecanoic acid and isooctadecanoic acid.

The partial ester is generally a monoester, diester, triester, tetraester, pentaester, or a mixture thereof, and in the case such a mixture is used the proportion of the various ester forms depends upon the kind of the carboxylic acid and the number of the hydroxyl groups of the polyhydric alcohol.

The partial esters which can be used in this invention can be used in the form of either a single partial ester or a mixture of partial esters which is formed in the synthesis of the partial esters. For example, when glycerin, trimethylolethane, or trimethylolpropane, which have 3 hydroxyl groups, are used, a mixture comprising a monoester is preferred; when diglycerin, pentaerythritol or sorbitan, which have 4 hydroxyl groups, are used, a mixture comprising a diester is preferred; and when sorbitol, which has 6 hydroxyl groups, is used, a mixture comprising a tetraester is preferred.

Particularly preferred examples of the partial esters used in this invention are glycerol mono-9-methylheptadecanoate, trimethylolpropane mono-9-methylheptadecanoate, pentaerythritol di-9-methylheptadecanoate, diglycerol di-9-methylheptadecanoate, glycerol monooleate, trimethylolpropane monooleate, diglycerol dioleate, pentaerythritol dioleate, diglycerol diricinolate, sorbitan dioleate, and sorbitan sesquioleate.

The amino acids or salts thereof used as an aqueous solution thereof in forming the water-in-oil emulsifier compositions of this invention are selected from the following amino acids and the salts thereof which are known as general additives for food and medical supplies. That is, L-alanine, β-alanine, glycine, L-serine, L-arginine hydrochloride, L-histidine hydrochloride, L-lysine hydrochloride, sodium L-aspartate monohydrate, potassium L-aspartate dihydrate, sodium L-glutamate monohydrate and potassium L-glutamate monohydrate. As a matter of course, D-isomers and DL-isomers of these amino acids or salts thereof can also be used in this invention.

The characteristics of these amino acids or salts thereof are as follows:

1. They have high solubility in water, for example, more than 20 g per 100 ml of water at 25° C.
2. They are within the range between 5 and 9 in their inorganic-organic balance (according to the definition of "Prediction of Organic Compounds by a Conoptional Diagram" as described by Atsushi Fujita; Chemical and Pharmaceutical Bulletin, 163-173 (1954)).

The concentration of the amino acid(s) or salt(s) thereof in the aqueous solution preferably ranges from about 0.1 to 40% by weight.

The water-in-oil emulsifier composition of this invention is obtained by mixing an aqueous solution of the amino acid or salt thereof having a proper concentration with a partial ester of a polyhydric alcohol and a fatty acid, and stirring the mixture until it is uniform.

In this case, it is desirable to add the aqueous solution of the amino acid or salt thereof to the fatty acid partial ester of a polyhydric alcohol with stirring until a uniform emulsion is obtained. Although it is generally known that the amino acids or salts thereof are readily decomposed or condensed by heating, in the emulsifier composition of this invention all operations can be performed at room temperature so that the amino acids or salts thereof contained in the emulsifier composition can be added without being denatured.

In this invention, an aqueous solution of the amino acid or the salt thereof having a higher concentration gives a most stable water-in-oil type emulsifier composition possessing slight transparency. However, an aqueous solution in a supersaturated state is not employed. For example, in the case of using sodium L-glutamate monohydrate, which is one of the most preferred embodiments of the amino acid salts, the desired novel water-in-oil emulsifier composition can be obtained by adding an aqueous solution of the amino acid salt having a concentration of 5 – 40%. If the concentration of the amino acid salt is higher than 40%, the product is not useful, while if the concentration is lower than about 5%, a water-in-oil type emulsion showing high fluidity is formed.

Furthermore, the mixing ratio of (A), the partial ester of the polyhydric alcohol and the fatty acid, and (B), the aqueous solution of the amino acid or a salt thereof, is properly selected. For example, in the case of employing a 5% aqueous solution of sodium L-glutamate monohydrate, the mixing ratio of component (B) to component (A) is 1 : 1 to 1 : 15 by weight, preferably in a range of from 1 : 2 to 1 : 10 by weight, while in the case of employing a 40% aqueous solution of the same amino acid salt, the mixing ratio is 1 : 1 to 1 : 46 by weight, preferably from 1 : 2 to 1 : 15 by weight. If an excessive amount of the aqueous solution of the amino acid or a salt thereof is added to the internal phase of the emulsion, this will cause phase separation of the emulsifier composition. As to amino acids or salts thereof other than the above-illustrated amino acid salts, the mixing ratio of component (B) to component (A) is selected properly in a certain range according to the solubility of the amino acids or the salts thereof, that is, the mixing ratio is generally from 1 : 1 to 1 : 46 by weight, preferably from 1 : 2 to 1 : 15 by weight.

The water-in-oil emulsifier compositions obtained by the present invention may be used to prepare water-in-oil type cosmetic preparations, such as cleansing creams (or lotions), emollient creams (or lotions), hand creams (or lotions), suntan preparations, foundation make-up, stick make-up, eye make-up preparations, ointments and the like, without using other emulsifiers. In the case of producing these water-in-oil type cosmetics or ointments, the novel emulsifier compositions of this invention are added to the oil phase of the above-described cosmetics in an amount of 5 – 30% by weight of the total emulsions or ointments. In this case, the cosmetic creams, stick cosmetics, milky lotions or ointments may contain additives as are conventionally used for cosmetics or ointments, such as fatty materials, such as mineral oils, vaseline, squalane, bees wax, ceresine, etc.; moisture-retaining agents, such as propylene glycol, glycerin, etc.; powders, such as talc, etc.; antiseptics, such as alkyl-p-hydroxybenzoate, isopropylmethylphenol, etc.; perfumes; metallic soaps, such as aluminum stearate, etc.; pigments; dyes; and the like, in conventional amounts.

The water-in-oil emulsifier compositions of this invention will be illustrated more in detail by the following examples, but the examples are for the sake of illustration only, not to limit the invention.

In the Examples all ratios are weight ratios and all percentages are weight percentages, unlss otherwise indicated. Further, all Examples were conducted at atmospheric pressure and at room temperature (about 25° C), unless otherwise indicated.

EXAMPLE 1

A water-in-oil emulsifier composition of this invention was prepared by mixing diglycerol di-9-methylheptadecanoate and a 40% aqueous solution of sodium L-glutamate at a mixing ratio of 1 : 2 (Sample No. A-1), 1 : 5 (Sample No. A-2), 1 : 9 (Sample No. A-3), or 1 : 15 (Sample No. A-4) with stirring.

EXAMPLE 2

A water-in-oil emulsifier composition of this invention was prepared by mixing glycerol monooleate and a 40% aqueous solution of sodium L-glutamate at a mixing ratio of 1 : 2 (Sample No. B-1), 1 : 5 (Sample No. B-2), 1 : 9 (Sample No. B-3), or 1 : 15 (Sample No. B-4), with stirring.

For the sake of comparison, a comparison sample was prepared by mixing glycerol monooleate and a 70% aqueous solution of sorbitol at a mixing ratio of 1 : 2 (Sample No. C-1), 1 : 5 (Sample No. C-2), 1 : 9 (Sample No. C-3), or 1 : 15 (Sample No. C-4) with stirring, which is corresponding to the case of U.S.P. 3,536,816.

A stability test of the water-in-oil type emulsifier compositions was then carried out on the water-in-oil emulsifier compositions of this invention (Sample Nos. A-1, A-2, A-3, A-4, B-1, B-2, B-3, and B-4) prepared in the above Examples and the comparison emulsifier compositions (Sample Nos. C-1, C-2, C-3, and C-4), i.e., one day and one month from the preparation of each sample, the hardness and the stability of each sample were measured.

The hardness of the sample was measured after one day and one month by means of a Card Tension Meter at a load of 200 g, and the reduction ratio in the hardness was determined.

The stability of the sample was evaluated by visual observation, in which a sample without phase separation was evaluated as grade 1 and a sample with high phase separation was evaluated as grade 5. The results are shown in the following table.

Table 1

| | Hardness | | Stability | | |
|---|---|---|---|---|---|
| | (1) After | (2) After | Reduction ratio $\frac{(1)-(2)}{(1)} \times 100\%$ | After | After |
| Sample | 1 day | 1 month | | 1 day | 1 month |
| A-1 | 12 | 7 | 41.7 | 2 | 2 |
| A-2 | 32 | 21 | 34.4 | 1 | 1 |
| A-3 | 48 | 32 | 33.3 | 1 | 1 |
| A-4 | 108 | 74 | 31.5 | 1 | 1 |
| B-1 | 8 | 8 | 0.0 | 2 | 3 |
| B-2 | 24 | 22 | 8.8 | 1 | 1 |
| B-3 | 33 | 28 | 15.2 | 1 | 1 |
| B-4 | 52 | 47 | 9.6 | 1 | 1 |
| C-1 | 13 | 1.5 | 88.5 | 2 | 5 |
| C-2 | 36 | 6 | 83.3 | 2 | 4 |
| C-3 | 72 | 11 | 84.7 | 2 | 3 |
| C-4 | 103 | 18 | 82.5 | 1 | 2 |

As is clear from the results shown in Table 1, comparison samples C-1, C-2, C-3, and C-4 showed a great reduction in hardness with the passage of time as compared with the samples of this invention A-1, A-2, A-3, A-4, B-1, B-2, B-3, and B-4, and further a tendency of phase separation was observed in the comparison samples.

A water-in-oil type cream sample was then prepared by blending 30% by weight of samples A-3, B-3 or C-3. The formulation of each cream was as follows:

| Squalane | 24% |
|---|---|
| Liquid Paraffin (Medium Viscosity; 126–334 Saybolt) | 5% |
| Ceresine | 1% |
| Bees Wax | 1% |
| Vaseline | 5% |
| Water-in-oil Emulsifier Composition | 30% |
| Water | 32.5% |
| Methyl-p-hydroxybenzoate | 0.5% |

The viscosity of each water-in-oil type cream was measured at the preparation of the emulsion (70° C) and upon cooling (30° C) after the preparation of the emulsion. The outward appearance of each cream and the stability of each cream after being allowed to stand for one month at 0°, 25° or 37° C were measured. The results are shown in Table 2.

Table 2

| | Viscosity | | Outward | Stability | | |
|---|---|---|---|---|---|---|
| Sample | (a)+ | (b)+ | Appearance | 0° C | 25° C | 37° C |
| A-3 | 13,900 cps | 101,600 cps | fine texture | 1 | 1 | 1 |
| B-3 | 12,500 cps | 94,430 cps | " | 1 | 1 | 3 |
| C-3 | 15,750 cps | 78,000 cps | coarse texture | 2 | 3 | 4 |

(a)+ at emulsification (70° C),
(b)+ after cooling (30° C)

As is clear from the results shown in Table 2, comparison sample C-3 showed a high viscosity at emulsification, and thus the sample was very hard to emulsify with a homomixer; further, the sample showed a great reduction in viscosity upon cooling. On the other hand, samples A-3 and B-3 had a proper viscosity for emulsification and upon cooling, and provided creams of high stability.

The cream containing sample C-3 furthermore had a coarse texture, and was undesirable for use.

EXAMPLE 3

| Trimethylolpropane Monooleate | 5.0 parts |
| L-Serine | 7.5 parts |
| Water | 17.5 parts. |

L-Serine was dissolved in the 17.5 parts of water and the aqueous solution thus prepared was mixed with trimethylolpropane monooleate with stirring to provide a water-in-oil emulsifier composition. The same procedure was followed in Examples 4 - 7 using the components as shown in each example below.

EXAMPLE 4

| Glycerol Monooleate (40% Monoglyceride) | 3.0 parts |
| Sodium L-Glutamate Monohydrate | 1.75 – 10.8 parts |
| Water | 26.25 – 16.2 parts |

EXAMPLE 5

| Diglycerol Di-9-methylheptadecanoate | 5.0 parts |
| Sodium L-Glutamate Monohydrate | 10.0 parts |
| L-Serine | 5.0 parts |
| Water | 35.0 parts |

EXAMPLE 6

| Diglycerol Dioleate | 5.0 parts |
| Sodium L-Glutamate Monohydrate | 2.0 – 46.0 parts |
| Water | 8.0 – 184.0 parts |

EXAMPLE 7

| Glycerol Monohydrate (40% Monoglyceride) | 4.0 parts |
| β-Alanine | 1.0 parts |
| Water | 7.0 parts |

The following formulations show cosmetics prepared using the water-in-oil emulsifier compositions of this invention prepared as above. It should be understood that these are only for illustration, and various changes can be made without departing from the spirit and scope of the present invention.

Formulation Example 1: Water-in-oil Type Cream (Nourishing Cream)

| Squalane | 24.5% by weight |
| Ceresine | 3.0% by weight |
| Bees Wax | 1.5% by weight |
| Lanolin | 0.5% by weight |
| Vaseline | 6.0% by weight |
| Water-in-oil Emulsifier composition in Example 5 | 24.0% by weight |
| Water | 34.3% by weight |
| Propylene Glycol | 5.0% by weight |
| Methyl-p-hydroxybenzoate | 0.5% by weight |
| Allantoin | 0.2% by weight |
| Perfume | 0.5% by weight |

The water-in-oil emulsifier composition was added to a mixture of squalane, ceresine, bees wax, lanolin, vaseline, methyl-p-hydroxybenzoate and the perfume, and then the mixture was heated to 70° C with stirring. Water, allantoin and propylene glycol heated to 70° C were then added to the mixture. Thereafter, the mixture was stirred for a few minutes at 70° C by means of a homomixer and then cooled to room temperature with stirring.

Formulation Example 2: Water-in-oil Type Cream (Hand Cream)

| Emulsifier Composition in Examples 1 – 7 | 10% by weight |
| Vaseline | 18.0% by weight |
| Mineral Oil (Medium Viscosity) | 36% by weight |
| Ceresine | 3.0% by weight |
| Multi Wax | 2.0% by weight |
| Water | 30.0% by weight |
| Butyl-p-hydroxybenzoate | 0.5% by weight |
| Perfume | 0.5% by weight |

The water-in-oil emulsifier composition was added to a mixture of vaseline, mineral oil, ceresine, multi wax, butyl-p-phydroxybenzoate, and the perfume, and then the mixture was heated to 70° C with stirring. Water heated to 70° C was then added to the mixture. Thereafter, the mixture was stirred for a few minutes (i.e., about 2 to 3 minutes) at 70° C by means of a homomixer and then cooled to room temperature with stirring.

Formulation Example 3: Water-in-oil Type Cream for Make-up

| Emulsifier Composition in Examples 1 – 7 | 30.0% by weight |
| Mineral Oil (Medium Viscosity) | 20.5% by weight |
| Bees Wax | 3.0% by weight |
| Ceresine | 1.0% by weight |
| Dry Powders (Titanium Dioxide, Inorganic Pigments and Talc) | 20.0% by weight |
| Aluminum Stearate | 0.5% by weight |
| Water | 24.0% by weight |
| Isopropylmethyl Phenol | 0.8% by weight |
| Perfume | 0.2% by weight |

The water-in-oil emulsifier composition was added to a mixture of the mineral oil, bees wax, ceresine, aluminum stearate, and isopropylmethyl phenol, and the perfume, and then the mixture was heated to 70° C with stirring. Then, the dry powders were added to the mixture and the resultant mixture was stirred well by means of a homomixer for a few minutes at 70° C. After adding water heated to 70° C to the resulting mixture, the resultant mixture was stirred again for an additional few minutes by means of a homomixer. The mixture was then cooled to room temperature with stirring.

Formulation Example 4: Stick Cosmetics (Water-Containing Stick)

| Ceresine | 20.0% by weight |
| Lanolin | 3.0% by weight |
| Mineral Oil (Heavy Viscosity; 335 – 365 Saybolt) | 50.0% by weight |
| Coloring Agents | 16.0% by weight |
| Emulsifier Composition in Examples 1 – 7 | 5.0% by weight |

| | |
|---|---|
| Water | 5.5% by weight |
| Perfume | 0.5% by weight |

A mixture of ceresine, lanolin, the mineral oil, the coloring agents, the water-in-oil emulsifier composition and the perfume was heated to 75° – 85° C with stirring and after adding the 5.5% of water, the mixture was stirred uniformly by means of a homomixer to emulsify the system and disperse the coloring agents. The resultant mixture was placed in a container and cooled to room temperature.

While specific examples of the formulations of the cosmetics of this invention are described above, it will be clear that the formulations and the concentrations of the components shown in the examples can be changed, and further the processing steps as illustrated can be modified within the scope of this invention described in the claims of this invention.

While the invention has been described in detail and with reference to specific embodiments thereof, it will be apparent to one skilled in the art that various changes and modifications can be made therein without departing from the spirit and scope thereof.

What is claimed is:

1. A water-in-oil emulsifier composition consisting essentially of:
   A. a partial ester of a polyhydric alcohol having 3 to 6 hydroxyl groups in the molecule and a fatty acid having 16 to 18 carbon atoms, which partial ester is in the liquid state at room temperature; and
   B. an aqueous solution containing at least one amino acid or salt thereof, said acid or salt having a solubility in water greater than 20g per 100 ml of water at 25° C and being between 5 and 9 in their inorganic-organic balance, said aqueous solution having a concentration of 0.1 to 40% by weight of said acid or salt;
   the mixing ratio of component (B) to component (A) being from 1:1 to 1:46 by weight.

2. A water-in-oil emulsifier composition consisting essentially of:
   A. a partial ester of a polyhydric alcohol having 3 to 6 hydroxyl groups in the molecule and a fatty acid having 16 to 18 carbon atoms, which partial ester is in the liquid state at room temperature; and
   B. an aqueous solution containing at least one water soluble amino acid or salt thereof selected from the group consisting of D-alanine, L-alanine, DL-alanine, β-alanine, glycine, D-serine, L-serine, DL-serine, D-arginine hydrochloride, L-arginine hydrochloride, DL-arginine hydrochloride, D-histidine hydrochloride, L-histidine hydrochloride, DL-histidine hydrochloride, D-lysine hydrochloride, L-lysine hydrochloride, DL-lysine hydrochloride, sodium D-aspartate monohydrate, sodium L-aspartate monohydrate, sodium DL-aspartate monohydrate, potassium D-aspartate dihydrate, potassium L-aspartate dihydrate, potassium DL-aspartate dihydrate, sodium D-glutamate monohydrate, sodium L-glutamate monohydrate, sodium DL- glutamate monohydrate, potassium D-glutamate monohydrate, potassium L-glutamate monohydrate and potassium DL-glutamate monohydrate, which aqueous solution has a concentration of 0.1 to 40% by weight of at least one amino acid or salt thereof, the mixing ratio of component (B) to component (A) being from 1:1 to 1:46 by weight.

3. The water-in-oil emulsifier composition as claimed in claim 2 wherein said polyhydric alcohol is a member selected from the group consisting of glycerin, diglycerin, trimethylolethane, trimethylolpropane, penetaerythritol, sorbitan and sorbitol.

4. The water-in-oil emulsifier composition as claimed in claim 2 wherein said fatty acid is iso-octadecanoic acid.

5. The water-in-oil emulsifier composition as claimed in claim 2 wherein said fatty acid is a member selected from the group consisting of oleic acid, linolic acid, ricinoleic acid and isohexadecanoic acid.

6. The water-in-oil emulsifier composition as claimed in claim 2 wherein said partial ester is diglycerol di-9-methylheptadecanoate.

7. The water-in-oil emulsifier composition as claimed in claim 2 wherein said partial ester is a member selected from the group consisting of glycerol mono-9-methylheptadecanoate, pentaerythritol di-9-methylheptadecanoate, trimethylolpropane, mono-9-methyldecanoate, glycerol di-9-methylheptadecanoate, glycerol monoleate, pentaerythritol dioleate, sorbitan dioleate, trimethylolpropane monooleate, diglycerol dioleate, diglycerol diricinolate and sorbitan sesqueoleate.

8. The water-in-oil emulsifier composition as claimed in claim 2 wherein said amino acid is L-serine and said amino acid salt is sodium L-glutamate monohydrate.

9. The water-in-oil emulsifier composition as claimed in claim 2 wherein a combination of L-serine and sodium L-glutamate is used as component (B).

10. The water-in-oil emulsifier composition as claimed in claim 2 wherein said mixing ratio is from 1:2 to 1:15 by weight.

11. The water-in-oil emulsifier composition of claim 2 wherein one or more amino acids are used.

12. The water-in-oil emulsifier composition of claim 2 wherein one or more amino acid salts are used.

13. The water-in-oil emulsifier composition of claim 2 wherein one or more amino acids plus one or more amino acid salts are used.

14. A cosmetic containing 5–30% by weight of the water-in-oil emulsifier composition claimed in claim 2.

15. A cosmetic containing the water-in-oil emulsifier composition comprisihg diglycerol di-9-methylheptadecanoate, L-serine, and sodium L-glutamate.

* * * * *